United States Patent
Janda

(10) Patent No.: US 11,083,502 B2
(45) Date of Patent: Aug. 10, 2021

(54) IMPLANTABLE BONE ADJUSTMENT DEVICE WITH A DYNAMIC SEGMENT

(71) Applicants: Smith & Nephew, Inc., Memphis, TN (US); Smith & Nephew Orthopaedics AG, Baar (CH); Smith & Nephew Pte. Limited, Singapore (SG)

(72) Inventor: Haden Janda, Cordova, TN (US)

(73) Assignees: Smith & Nephew, Inc., Memphis, TN (US); Smith & Nephew Orthopaedics AG, Zug (CH); Smith & Nephew Pte. Limited, Singapore (SG)

( * ) Notice: Subject to any disclaimer, the term of this patent is extended or adjusted under 35 U.S.C. 154(b) by 75 days.

(21) Appl. No.: 16/540,231

(22) Filed: Aug. 14, 2019

(65) Prior Publication Data

US 2020/0054371 A1 Feb. 20, 2020

Related U.S. Application Data

(60) Provisional application No. 62/718,671, filed on Aug. 14, 2018.

(51) Int. Cl.
*A61B 17/72* (2006.01)

(52) U.S. Cl.
CPC ................ *A61B 17/7216* (2013.01)

(58) Field of Classification Search
CPC . A61B 17/7216; A61B 17/7225; A61B 17/72; A61B 17/7016; A61B 17/7014; A61B 17/7017
See application file for complete search history.

(56) References Cited

U.S. PATENT DOCUMENTS

| 4,611,582 | A  | * | 9/1986 | Duff ................. A61B 17/7047 606/258 |
| 6,730,087 | B1 | * | 5/2004 | Butsch .............. A61B 17/7216 606/105 |
| 8,777,947 | B2 |   | 7/2014 | Zahrly et al. |
| 9,421,046 | B2 |   | 8/2016 | Pool et al. |
| 10,722,278 | B2 |   | 7/2020 | Janda et al. |

(Continued)

FOREIGN PATENT DOCUMENTS

WO 2006079184 A1 8/2006
WO 2008129995 A1 10/2008

*Primary Examiner* — Julianna N Harvey
(74) *Attorney, Agent, or Firm* — Kacvinsky Daisak Bluni PLLC

(57) ABSTRACT

A reconfigurable bone adjustment device includes a first member configured for attachment to a first bone fragment, portion, etc., a second member configured for attachment to a second bone fragment, portion, etc., a drive mechanism configured to move the second member relative to the first member, a threaded rod having a proximal end operatively coupled to the drive mechanism and a distal end operatively coupled to the second member so that rotation of the drive mechanism rotates the threaded rod and moves the second member relative to the first member, and a dynamic segment positioned between the first and second members to enable compression of the second member relative to the first member to stimulate bone growth. The dynamic segment may be a silicone/rubber compressible member or assembly, a metallic spring, a non-metallic shock absorbing material or washer, or the like.

10 Claims, 5 Drawing Sheets

(56) References Cited

U.S. PATENT DOCUMENTS

| | | | |
|---|---|---|---|
| 2004/0030395 A1* | 2/2004 | Blunn | A61B 17/7216 623/18.12 |
| 2005/0246034 A1* | 11/2005 | Soubeiran | A61B 17/7216 623/23.45 |
| 2012/0136356 A1* | 5/2012 | Doherty | A61B 17/7225 606/62 |
| 2019/0326043 A1 | 10/2019 | Janna et al. | |
| 2019/0336183 A1 | 11/2019 | Farley et al. | |
| 2020/0022741 A1 | 1/2020 | Janda et al. | |

* cited by examiner

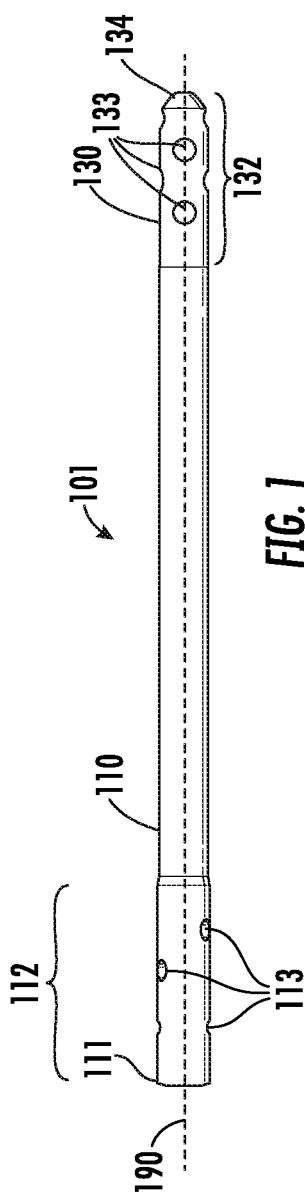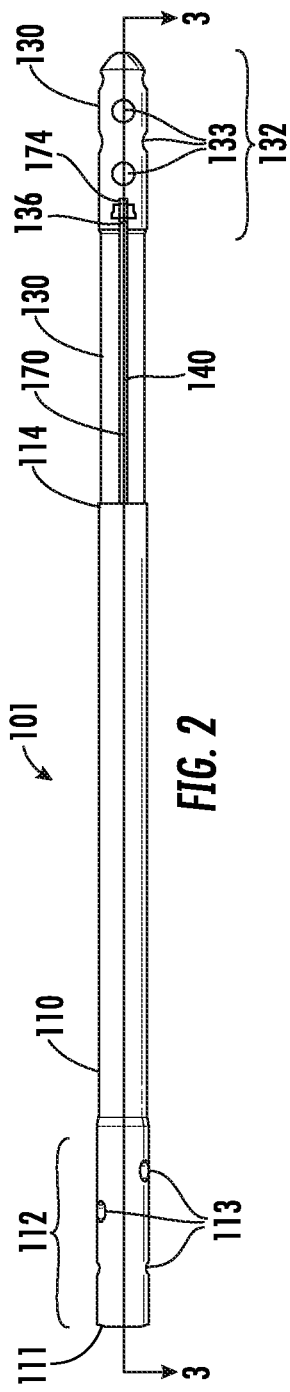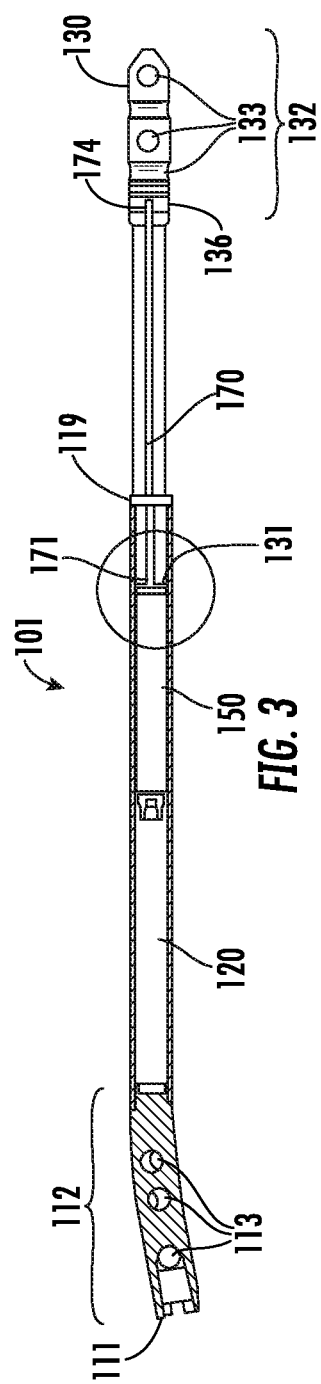

IMPLANTABLE BONE ADJUSTMENT DEVICE WITH A DYNAMIC SEGMENT

CROSS-REFERENCE TO RELATED APPLICATION

This application claims the benefit of U.S. Provisional Patent Application Ser. No. 62/718,671, filed Aug. 14, 2018, entitled Implantable Bone Adjustment Device with a Dynamic Segment, the entire contents of which application is hereby incorporated by reference in its entirety.

TECHNICAL FIELD

The present disclosure generally relates to implantable reconfigurable bone adjustment devices such as, for example, intramedullary limb lengthening nails, and more particularly, but not exclusively, relates to implantable reconfigurable bone adjustment devices that included a dynamic segment (e.g., a compressible member, assembly, portion, or the like).

BACKGROUND

Implantable reconfigurable bone adjustment devices are occasionally used in orthopedic procedures to gradually adjust the position, orientation, geometry and/or length of a bone, such as, for example, by distraction, compression, realignment or bone transport. One form of an implantable reconfigurable bone adjustment device is a limb lengthening nail (LLN) configured for implantation in the medullary canal of a long bone and subsequently manipulated to adjust the length of the bone. Another form of an implantable reconfigurable bone adjustment device is a bone transport nail configured for implantation in the medullary canal of a long bone and subsequently manipulated to move a middle bone fragment across a gap between proximal and distal bone fragments to induce bone regeneration in the gap. Still other forms of implantable reconfigurable bone adjustment devices include spinal adjustment implants and implants configured to achieve other gradual adjustments to the shape, position or length of skeletal structures.

Implantable reconfigurable bone adjustment devices may include a drive mechanism such as, for example, internal magnets that are configured to rotate upon actuation by an external actuating device such as, for example, an external magnet, thereby driving a threaded rod that engages other device components to achieve a dimensional modification of the device or other relational modification between components of the device. Such dimensional modification or relational modification of the device operate on bone segments, portions or fragments to which the device is affixed to exert pressures on the bone segments, portions or fragments to which the device is affixed, thereby gradually moving the bone segments, portions or fragments relative to one another. Such devices may include a first member configured to be affixed to a first bone segment, portion or fragment; a second member configured to be affixed to another bone segment, portion or fragment; a rod with at least one thread, the rotation of which causes displacement of the second member relative to the first member, and a drive mechanism for controlling the rotation of the threaded rod. In the case of certain LLN devices, for example, the second member may be assembled telescopically relative to the first member and rotation of the threaded rod operates to telescopically displace the second member relative to the first member, thereby increasing the distance between the bone segments, portions or fragments to which the first member and the second member are respectively affixed.

While currently-available bone adjustment devices have produced excellent results, many of these devices exhibit one or more shortcomings or disadvantages that render the device susceptible to failure. For example, one common drawback associated with implantable reconfigurable bone adjustment devices (e.g., LLN nails) is their reduced or limited weight bearing capability. That is, for example, LLN nails are telescopic in nature and thus weaker than a tradition intramedullary nail used in trauma applications. As a result, efforts are being made to design and develop LLN nails that are stronger and thus capable of withstand greater weight bearing. However, as LLN nails are designed and developed to withstand greater weight bearing, other drawbacks may occur. For example, if an LLN nail is too rigid, the stiffness of the nail may be increased beyond an optimal point for adequate bone regeneration and consolidation during lengthening. As a result, excessive stress shielding may occur that prevents or delays the treatment goals. For these reasons among others, a need remains for further improvements in this technological field. The present disclosure addresses this need.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a reconfigurable bone adjustment device comprising: a first member configured for attachment to a first bone fragment; a second member configured for attachment to a second bone fragment; a drive mechanism configured to move the second member relative to the first member; a threaded rod having a proximal end operatively coupled to the drive mechanism, and a distal end operatively coupled to the second member so that operation (e.g., rotation) of the drive mechanism rotates the threaded rod and moves the second member relative to the first member; and a dynamic segment positioned between the first and second members to enable compression of the second member relative to the first member to stimulate bone growth.

In some embodiments, the dynamic segment is positioned within the first body member.

In some embodiments, the dynamic segment is positioned adjacent to the drive mechanism.

In some embodiments, the dynamic segment is a metallic spring. In some embodiments, the metallic spring is selected from one of a wave spring, a domed disc, Belleville spring, and a multi-wave spring. In some embodiments, the metallic spring is arranged in one of a single stack, parallel stacks, series stacks, or parallel-series stacks.

In some embodiments, the dynamic segment is a non-metallic shock absorbing washer.

In some embodiments, the dynamic segment is a non-metallic shock absorbing member. In some embodiments, the non-metallic shock absorbing member is selected from one of a silicone or urethane washer.

In some embodiments, the dynamic segment includes a compressible member. In some embodiments, the compressible member is selected from one of a silicone and a rubber.

In some embodiments, the dynamic segment includes a compressible assembly. In some embodiments, the compressible assembly includes a compressible member sandwiched between first and second end plates. In some embodiments, the compressible member is selected from one of a silicone and a rubber, and the end plates are manufactured from a metallic material. In some embodiments, the compressible member is molded to the end plates. In some embodiments, the compressible assembly including the compressible member and the first and second end plates include an opening formed therein for enabling the threaded rod to pass therethrough.

In some embodiments, the dynamic segment includes a containment cup and a compressible member. In some embodiments, the containment cup includes a ledge projecting along an outer circumference thereof, the ledge defining a pocket arranged and configured to receive at least a portion of the compressible member therein. In some embodiments, the containment cup is manufactured from a metallic material, the compressible member is manufactured from one of a silicone or a rubber. In some embodiments, the compressible member extends beyond the ledge of the containment cup.

Embodiments of the present disclosure provide numerous advantages. For example, by incorporating, providing, etc. a dynamic segment between the first and second members of a reconfigurable bone adjustment device, movement of the first and second members relative to each other is enable. Thus arranged, bone growth may be stimulated. In addition, stress shielding may be prevented.

Further features and advantages of at least some of the embodiments of the present invention, as well as the structure and operation of various embodiments of the present invention, are described in detail below with reference to the accompanying drawings.

BRIEF DESCRIPTION OF THE FIGURES

FIG. 1 illustrates a side view of an example of an embodiment of an intramedullary limb lengthening nail, the limb lengthening nail illustrated in a retracted or contracted state;

FIG. 2 illustrates a side view of the intramedullary limb lengthening nail shown in FIG. 1, the limb lengthening nail illustrated in an extended or distracted state;

FIG. 3 illustrates a cross-sectional view of the limb lengthening nail shown in FIG. 2, taken along line 3-3;

Figure 4:
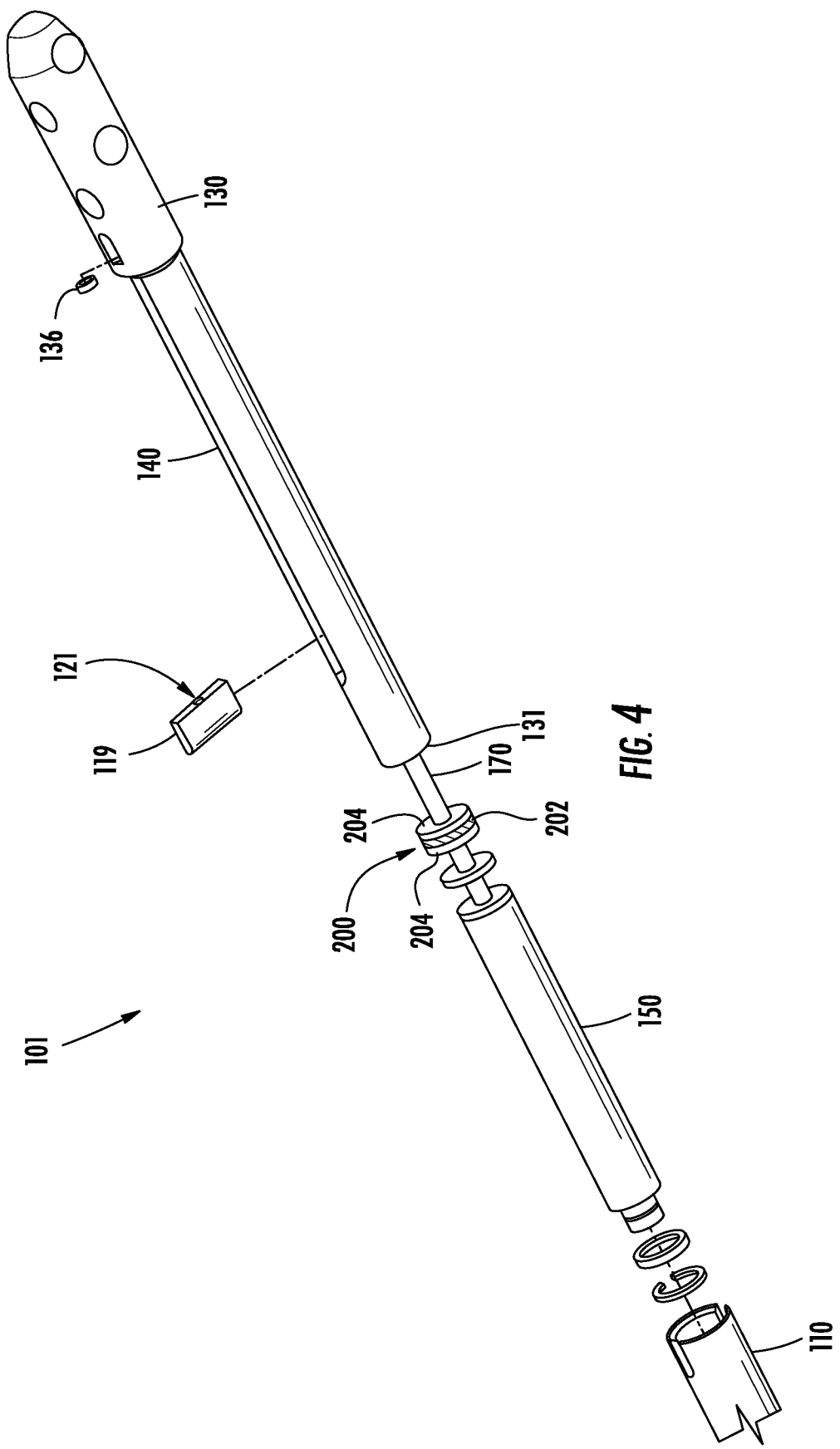
FIG. 4 illustrates a partially, exploded view of an example of an embodiment of an intramedullary limb lengthening nail in accordance with one aspect of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

For the purposes of promoting an understanding of the principles of the present disclosure, reference will now be made to the embodiments illustrated in the figures and specific language will be used to describe the same. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

Various implantable reconfigurable bone adjustment devices are disclosed herein. In one embodiment, the implantable reconfigurable bone adjustment device may include a first member, body portion or component (used interchangeably herein without the intent to limit), a second member, and a rotatable threaded rod that engages at least one component affixed to the first member and at least one component operable to axially move the second member relative to the first member. The implantable reconfigurable bone adjustment device may also include a drive mechanism to controllably actuate rotation of the threaded rod. In certain embodiments, the drive mechanism may be an internal magnet coupled to the threaded rod such that rotation of the internal magnet drives rotation of the threaded rod. This can be achieved, for example, by fixing the threaded rod directly to the internal magnet or a housing in which the internal magnet is contained or can be achieved by connecting the threaded rod indirectly to the internal magnet, such as through a gear mechanism or other structure positioned therebetween. As described further herein, torque may be applied to the internal magnet by applying a rotating magnetic field across the internal magnet from an external source. In other implantable reconfigurable bone adjustment device embodiments, rotation of the threaded rod may be controlled or driven by a drive mechanism other than an internal magnet. Alternative drive mechanisms for driving the threaded rod may include any other now known or hereafter developed drive mechanisms known to a person of ordinary skill in the art, including, for example, an electric motor with or without gear reduction, a current source inside or outside the patient's body, a permanent magnet with a gear reducer and a rotating magnetic field source external to the patient, etc. In alternate embodiments, the drive mechanism can be configured to drive the threaded rod in one direction only, or in both directions, according to requirements. The first and second body portions are dimensioned such that the body portions can move in at least one axial direction with respect to one another upon rotation of the threaded rod. For additional information on the components, operation, features, etc. of various representative, but non-limiting, examples of implantable reconfigurable bone adjustment devices contemplated by the present disclosure reference is hereby made to U.S. patent application Ser. Nos. 16/473,961 entitled Bone Transport Nail; 16/473,942 entitled Actuation System and Method for Orthopedic Implants with a Rotatable Internal Magnet; 16/142,269 entitled Implantable Bone Adjustment Devices; and PCT international Patent Application No. PCT/US18/15731 entitled Implantable Bone Adjustment Devices, the contents of each application is hereby incorporated by reference in its entirety.

One representative, but non-limiting, example, of an implantable reconfigurable bone adjustment device contemplated by the present disclosure is an intramedullary limb lengthening nail, such as intramedullary ("TM") limb lengthening nail 101 depicted in FIGS. 1-3. Further details regarding representative TM limb lengthening nails are available in U.S. Pat. No. 8,777,947, which is hereby incorporated herein by reference in its entirety. Referring to FIGS. 1-3, the TM limb lengthening nail 101 may include a proximal body portion 110, a distal body portion 130, and a threaded rod 170 operatively associated with the proximal body portion 110 and the distal body portion 130. In use, rotation of the threaded rod 170 causes the proximal body portion 110 and the distal body portion 130 to move with respect to one another. In one embodiment, as will be described in greater detail, the proximal body portion 110 may be configured as an outer body and the distal body portion 130 may be configured as an inner body so that at least a portion of the distal body portion 130 may be received within the proximal body portion 110. Alternatively, it is envisioned that the proximal body portion 110 may be configured as the inner body and the distal body portion 130 may be configured as the outer body. In one embodiment, the threaded rod 170 may be mounted in and coupled to the distal body portion 130.

Each of the proximal body portion 110, distal body portion 130, and threaded rod 170 has a proximal end 111, 131, 171 and a distal end 114, 134, 174, respectively. The IM limb lengthening nail 101 may also include a drive mechanism for driving rotation of the threaded rod 170. In use, actuation of the drive mechanism is controlled to achieve a desired amount of rotation over time and at a desired rate, thereby achieving a desired amount of bone adjustment at a desired rate. In certain devices, the drive mechanism includes a magnet hermetically sealed in a housing, although other types of drive mechanisms, such as electric motors, are contemplated. That is, the IM limb lengthening nail 101 includes an inner magnet 150 (also referred to herein as "internal magnet") seated in the proximal body portion 110 and coupled, either directly or indirectly, to the proximal end 171 of the threaded rod 170. A distal end 174 of the threaded rod 170 may be coupled to a distal block 136, which is coupled to the distal body portion 130. The IM limb lengthening nail 101 may also include a threaded block 119 coupled to the proximal body portion 110 and engaged with the threaded rod 170.

The term "inner" or "internal" is used herein in reference to the magnet 150 positioned within the implantable reconfigurable bone adjustment device 101 to distinguish this magnet from a different magnet or multiple different magnets employed by an external actuator as described in greater detail below, which magnet or magnets of an external actuator, are referred to as "outer magnets." While neodymium magnets are suggested, other magnets may be employed as will be apparent to those skilled in the art.

In use, the distal body portion 130 includes an elongated slot 140 which enables the threaded block 119 to slide along the distal body portion 130 during relative movement of the proximal and distal body portions 110, 130 along the longitudinal axis 190. That is, the threaded rod 170 is threadably coupled to the threaded block 119, which is fixedly coupled to the proximal body portion 110 (e.g., the threaded block 119 may be, for example, laser welded to the proximal body portion 110). Thus, in use, rotation of the internal magnet 150 causes the threaded rod 170 to rotate, which causes the distal body portion 130 to move relative to the proximal body portion 110. As the distal body portion 130 moves relative to the proximal body portion 110, the slot 140 formed in the distal body portion 130 moves relative to the threaded block 119. It should be appreciated that this is but one example embodiment, other embodiments are envisioned, so long as operation of the drive mechanism moves the proximal and distal body portions 110, 130 relative to each other.

The proximal body portion 110 may be at least partially hollow, having an inner wall 120 that defines an internal cylindrical chamber, for accommodating a portion of the distal body portion 130, which extends through the distal end 114 of the proximal body portion 110. The proximal and distal body portions 110, 130 are dimensioned such that the proximal and distal body portions 110, 130 can move in both axial directions with respect to one another. The proximal body portion 110 may also house the inner magnet 150, which may be mounted in a housing or carrier to facilitate the coupling of the inner magnet 150 to the threaded rod 170. The inner magnet 150 may include at least one permanent magnet, one of the poles of which is directed in one radial direction relative to a longitudinal axis 190 of the IM limb lengthening nail 101 and the other pole directed in an opposite radial direction relative to the longitudinal axis 190. As will be appreciated by one of ordinary skill in the art, the inner magnet 150 may be rotated about the longitudinal axis 190 of the IM limb lengthening nail 101 by application of an externally applied rotating magnetic field. The IM limb lengthening nail 101 may also include a first locking portion 112 and a second locking portion 132, each of which includes a plurality of fastener openings 113, 133 structured to receive fasteners for coupling the respective ends of the IM limb lengthening nail 101 to the patient's bone.

The inner magnet 150 is coupled, either directly or indirectly, to the threaded rod 170, which extends through the proximal end 131 of the distal body portion 130. The threaded rod 170 may also extend through a bearing (not shown) which engages the inner wall 120 of the proximal body portion 110. Similarly, a bearing may be coupled to a proximal end of the inner magnet 150 to facilitate rotation of the inner magnet 150 within the proximal body portion 110. The distal end 174 of the threaded rod 170 is engaged with the distal block 136, which is coupled to the distal body portion 130. In use, the distal block 136 permits rotation of the threaded rod 170 with respect to the distal body portion 130 and couples the distal body portion 130 and the threaded rod 170 for joint movement along the longitudinal axis 190. For example, the distal block 136 may be coupled or affixed to the distal body portion 130 such that the threaded rod 170 can rotate freely without altering the position of the distal end 174 of the threaded rod 170 with respect to the distal body portion 130. The threaded rod 170 also extends through the threaded block 119, which is coupled to the proximal body portion 110.

The threaded rod 170 may include a set of external threads which engage with a set of internal threads formed in a threaded bore 121 (FIG. 4) formed in the threaded block 119. As noted above, the threaded rod 170 is axially coupled to the distal body portion 130 via the distal block 136 and is axially and rotationally coupled to the inner magnet 150. In addition, the threaded rod 170 is threadably engaged with the threaded block 119, which is axially and rotationally coupled to the proximal body portion 110. As a result, rotation of the inner magnet 150 causes relative movement of the proximal and distal body portions 110, 130 along the longitudinal axis 190. Once again, it should be appreciated that this is but one example embodiment, other embodiments are envisioned, so long as operation of the drive mechanism moves the proximal and distal body portions 110, 130 relative to each other.

FIG. 1 illustrates the IM limb lengthening nail 101 in a retracted or contracted state, and FIGS. 2 and 3 illustrate the IM limb lengthening nail 101 in an extended or distracted state. The IM limb lengthening nail 101 may be moved between the contracted and distracted states by rotating the inner magnet 150 by application of an externally applied rotating magnetic field. More specifically, rotation of the inner magnet 150 may cause rotation of the threaded rod 170 resulting in movement of the distal body portion 130 relative to the proximal body portion 110 along the longitudinal axis 190, thereby adjusting the length of the IM limb lengthening nail 101. As is evident from a comparison of FIGS. 2 and 3, the longitudinal positions of the distal block 136 and the distal end 174 of the threaded rod 170 with respect to the distal body portion 130 remain unchanged. That is, the elongated slot 140 formed in the distal body portion 130 enables the threaded block 119 to slide along the distal body portion 130 during relative movement of the proximal and distal body portions 110, 130 along the longitudinal axis 190.

In use, the IM limb lengthening nail 101 is configured for implantation in a bone having a medullary canal. Typically, the IM limb lengthening nail 101 is implanted such that the first locking portion 112 is affixed to a first bone portion and the second locking portion 132 is affixed to a second bone portion, and a gap separates the first and second bone portions. The gap may be formed, for example, during an osteotomy procedure in which the bone is severed for purposes of lengthening the bone over time. The IM limb lengthening nail 101 is implanted into the medullary canal of the bone and is surgically coupled to the bone. For example, the proximal body portion 110 is coupled to the first bone portion and the distal body portion 130 is coupled to the second bone portion by fasteners such as screws or pins, which may be received in or otherwise engaged with the openings 113, 133.

Both distraction and compaction of the proximal and distal body portions 110, 130 with respect to each other is possible. Thus, with the IM limb lengthening nail 101 implanted in the bone, the segmented portions of the bone may be distracted or compacted as necessary by rotation of the threaded rod 170 and the inner magnet 150 in a first direction or a second direction, respectively, thereby enabling lengthening or shortening of the bone. In other words, the telescoping ability allows the IM limb lengthening nail 101 to both distract and contract the bone portions, to which the proximal and distal body portions 110, 130 are coupled. During lengthening, the IM limb lengthening nail 101 may be transitioned from the retracted state (FIG. 1) to the expanded state (FIG. 2), thereby lengthening the bone. The IM limb lengthening nail may be transitioned from the retracted state to the expanded state gradually over a given period of time, such that an ossified region forms as the bone lengthens and heals.

It should be understood that the principles and features of the present disclosure are not limited to use with the IM limb lengthening nail illustrated and described in connection with FIGS. 1-3 and that the principles and features of the present disclosure may be used in combination with other implantable reconfigurable bone adjustment devices such as, for example, other limb lengthening devices, an IM bone transport nail, or the like. In addition, it is to be understood that the present disclosure in not limited to use with in an implantable reconfigurable bone adjustment device, it being understood that the principles and features of the present disclosure find advantageous use with a variety of other reconfigurable bone adjustment devices that include a drive mechanism operable to controllably rotate a driver (e.g., internal magnet) that is coupled to a threaded rod to drive rotation of the threaded rod to move first and second members of the device relative to one another.

In one example embodiment, as will be readily appreciated by one of ordinary skill in the art, during operation, as indicated above, to rotate the threaded rod 170, a rotating magnetic field is applied to the device 101 to apply torque to the internal magnet 150. In one embodiment, this torque is applied by magnetically coupling an external magnetic actuator with the internal magnet 150.

The creation of a magnetic driving field for rotating the internal magnet 150 and the threaded rod 170 coupled coaxially therewith can be accomplished by a wide variety of mechanisms. In one manner of actuating rotation of the internal magnet 150 following implantation of an implantable reconfigurable bone adjustment device 101 in a skeletal position of a patient, an external magnetic actuator, also referred to herein as an actuation unit may be used. In one embodiment, the external magnetic actuator is operable to position a driving magnet, also referred to herein as an outer magnet, near the implanted device 101, but external to the patient, at the height of the internal magnet 150. The external magnetic actuators are designed and positioned to maximize torque to the internal magnet 150 and the threaded rod 170 and, in any event, to provide sufficient torque to rotate the internal magnet 150 despite the distance between the internal magnet 150 and the one or more outer magnets in the external magnetic actuator and applied resisting forces on the device 101. In this regard, rotation of the internal magnet 150 must overcome any compressive load imparted between the components of the device 101 by bone tissue and other tissues of the patient, together with internal frictional forces of the device 101.

In the presence of a magnetic driving field perpendicular to the rotational axis of the internal magnet 150 (which lies on the longitudinal axis 190 in the respective embodiments) and rotating around this axis, the internal magnet 150 tends to become oriented in the magnetic driving field, which applies a torque to the internal magnet 150 and causes the internal magnet 150 to rotate in the same rotational direction of the magnetic driving field, together with threaded rod 170 that is coupled coaxially with internal magnet 150, if the applied torque is greater than the load torque on threaded rod 170 under the load applied to it at the time when the magnetic driving field is activated.

In one embodiment, the driving magnet comprises at least one permanent magnet, one of the poles of which is directed towards longitudinal axis 190. In another embodiment, an even greater torque can be applied to the internal magnet 150 by using two permanent driving magnets positioned such that the south pole of one is facing the north pole of the other, and such that the implanted device and the part of the patient's body that surrounds the implanted device are positioned between the two permanent magnets.

As previously mentioned, one common problem associated with IM limb lengthening nails is as they are designed and developed to withstand greater weight bearing, stiffness of the nail may be increased beyond an optimal point for adequate bone regeneration. That is, by increasing stiffness of the nail through design and materials, excessive stress shielding may occur at the regenerated area that delays, or prevents, the achievement of the lengthening treatment goals.

In accordance with one aspect of the present disclosure, the IM limb lengthening nail 101 includes a dynamic portion, segment, component, assembly, or the like (terms used interchangeably herein without the intent to limit). In use, the dynamic segment 200 is adapted and configured to compress during use, resulting in axial movement of the nail 101 to stimulate bone growth. That is, during weight bearing, as compression is imparted onto the nail 101, compression of the dynamic segment 200 results in axial movement of the proximal and distal body portions 110, 130 of the nail 101 relative to each other to stimulate bone growth (e.g., the distal and proximal portions 110, 130 of the nail 101 compress together, which enable compression of the distal and proximal sections of the bone as the bone portions are fixed to the nail 101). Axial load sharing between the nail 101 and the regenerated bone is achieved thereby preventing or limiting non-union and potentially speed up consolidation.

As a result, incorporation of the dynamic or compressible segment 200 enables the IM limb lengthening nail 101 to be designed for optimized strength, while allowing for axial compression during weight bearing to promote load sharing between the regenerated area and the IM limb lengthening nail 101 to stimulate bone growth. In one embodiment, the dynamic segment 200 is adapted and configured to promote axial compression while avoiding transverse or torsional movement.

In addition, during extraction, as soft tissue is lengthened, the tissue forces may react to the nail 101 in a viscoelastic nature. The viscoelastic effect can be characterized by a rate-dependent linear spring and dashpot model, where the force required to lengthen the soft tissue is time dependent. As a result, an instantaneous movement caused by, for example, lengthening of the IM limb lengthening nail 101 could result in a large instantaneous force being required to distract the nail 101. Incorporation of the dynamic segment 200 may also assist with dampening any instantaneous lengthening movements and thus reduce the force required to distract the soft tissue, resulting in a more efficient nail.

Figure 5:
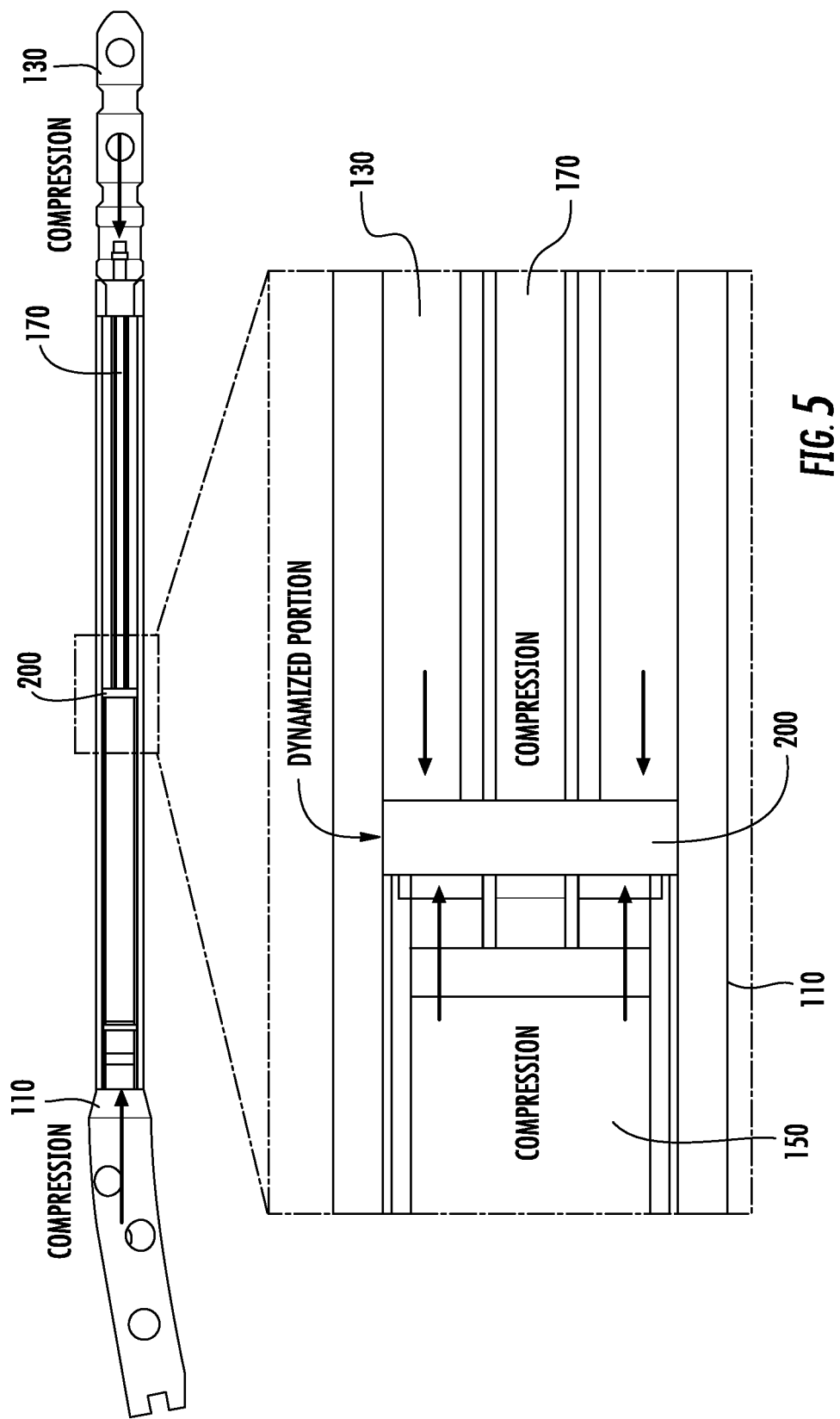
FIG. 5 illustrates various cross-sectional views of the intramedullary limb lengthening nail shown in FIG. 4.

Referring to FIGS. 4 and 5, in accordance with one principle of the present disclosure, the IM limb lengthening nail includes a dynamic segment 200 to enable axial compression of the nail (e.g., enable axial movement of the proximal and distal body portions 110, 130 of the nail relative to each other). As illustrated, in one example embodiment, the dynamic segment 200 may be positioned or located between the proximal body portion 110 and the distal body portion 130. For example, as illustrated, the dynamic segment 200 may be positioned or contained within the proximal body member 110 such as, for example, positioned or located adjacent to the internal magnet 150 contained within the proximal body portion 110 and adjacent to the proximal end 131 of the distal body portion 130 when the nail is a retracted state. By positioning the dynamic segment 200 within the proximal body portion 110, transverse or torsional movement is prevented or at least limited. In use, the dynamic segment 200 enables a small amount of axial translation between the proximal body portion 110 and the distal body portion 130 to promote bone regeneration (e.g., the dynamic segment 200 enables a small amount of axial compression during weight bearing while preventing shear or rotational movement).

The dynamic segment 200 may be any suitable mechanism, assembly, component, or the like that allows the proximal body portion 110 and the distal body portion 130 to axially translate relative to one another. For example, as illustrated in FIG. 4, the dynamic segment 200 may be in the form of a compressible member 202. The compressible member 202 may be formed from any suitable material now known or hereafter developed and may have any suitable configuration now known or hereafter developed for enabling the proximal body portion 110 and the distal body portion 130 to axially move relative to each other. In one embodiment, as illustrated, the dynamic segment 200 may be in the form of a compressible member 202 sandwiched between two end plates 204. The compressible member 202 may be manufactured from, for example, silicone, rubber, etc., although other suitable materials are envisioned. The end plates 204 may be manufactured from, for example, metals, although other suitable materials are envisioned. In use, the compressible member (e.g., silicone, rubber, etc.) 202 may be coupled to the end plates 204 by any suitable means now known or hereafter developed including, for example, adhesives, fasteners, etc. In one embodiment, the compressible member (e.g., silicone, rubber, etc.) 202 may be molded to the end plates 204. Thus arranged, the compressible member (e.g., silicone, rubber, etc.) 202 and the end plates 204 are arranged and configured as a single assembly, as opposed to three separate components. As illustrated, the dynamic segment 200 including the compressible member 202 and end plates 204 may all include an opening formed therein for enabling the threaded rod 170 to pass therethrough, although other suitable mechanisms for holding, positioning, etc. the dynamic segment 200 between the proximal body portion 110 and the distal body portion 130 are envisioned.

Figure 6A:
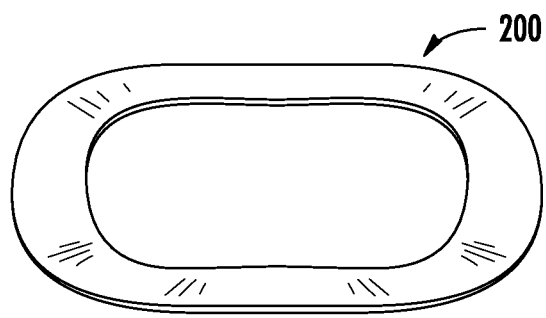
FIGS. 6A-6C illustrate various perspective views of alternate examples of a dynamic segment that may be used in connection with the intramedullary limb lengthening nail shown in FIGS. 4 and 5, the dynamic segment being in the form of a spring type member.
Figure 6B:
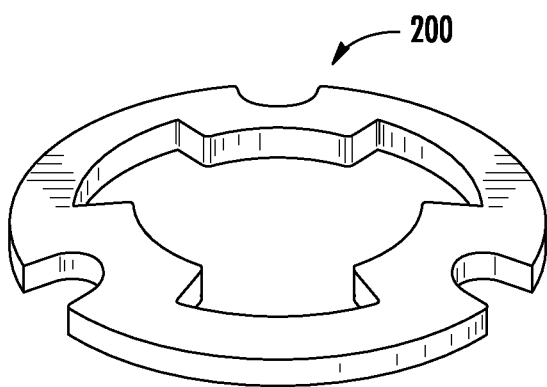
Figure 6C:
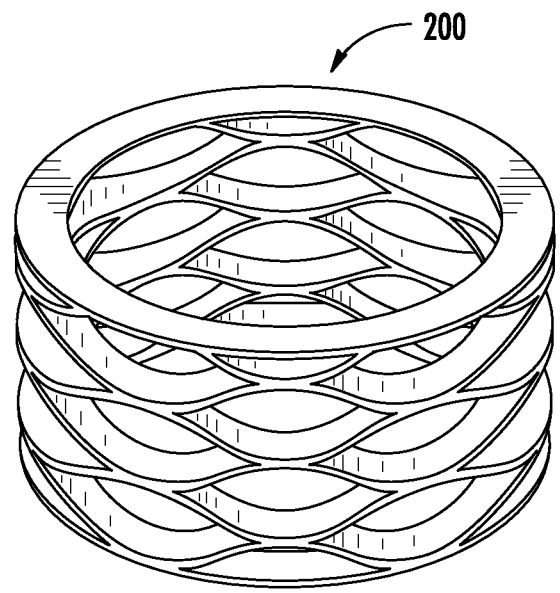
Figure 7:
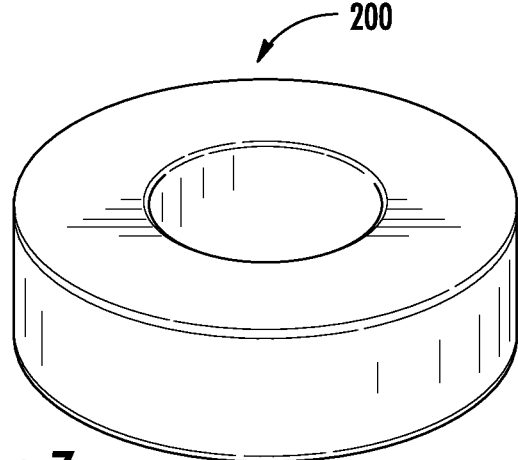
FIG. 7 illustrates a perspective view of an alternate example of an embodiment of a dynamic segment that may be used in connection with the intramedullary limb lengthening nail shown in FIGS. 4 and 5, the dynamic segment being in the form of an elastomeric member.

Alternatively, for example, referring to FIGS. 6A-6C, in an alternate embodiment, the dynamic segment 200 may be a metallic spring such as, for example, a wave spring, a domed disc, a Belleville spring, a multi-wave spring, or the like. The springs may be used singly or in parallel stacks, series stacks, or parallel-series stacks. In use, the required force to compress the dynamic segment 200 can be fine-tuned based on various spring constants, number of springs, or type of spring stack. Alternatively, referring to FIG. 7, the dynamic segment 200 may be formed from or as a non-metallic shock absorbing material or washer. For example, the dynamic segment 200 may be a non-metallic material, such as a silicone or urethane washer. In use, the required force to compress the non-metallic dynamic segment can be fine-tuned based on various material durometers.

Figure 8A:
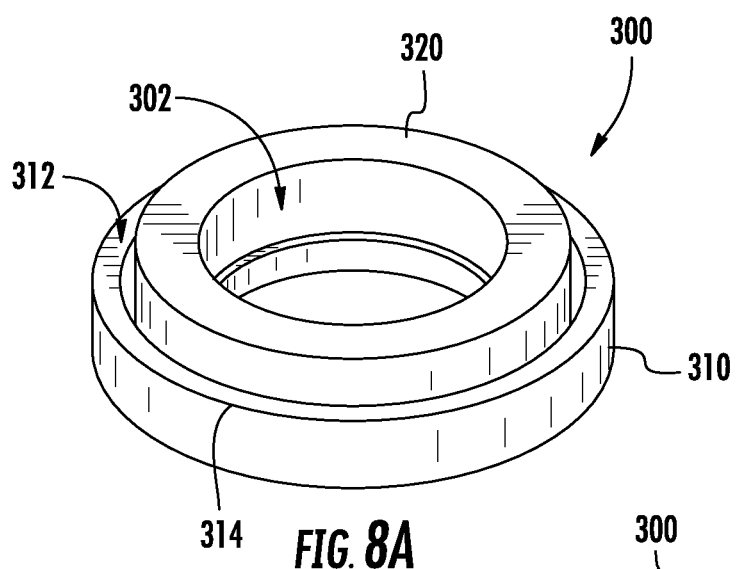
FIG. 8A illustrates a perspective view of an alternate example of an embodiment of a dynamic segment that may be used in connection with the intramedullary limb lengthening nail shown in FIGS. 4 and 5, the dynamic segment being in the form of a compressible member.
Figure 8B:
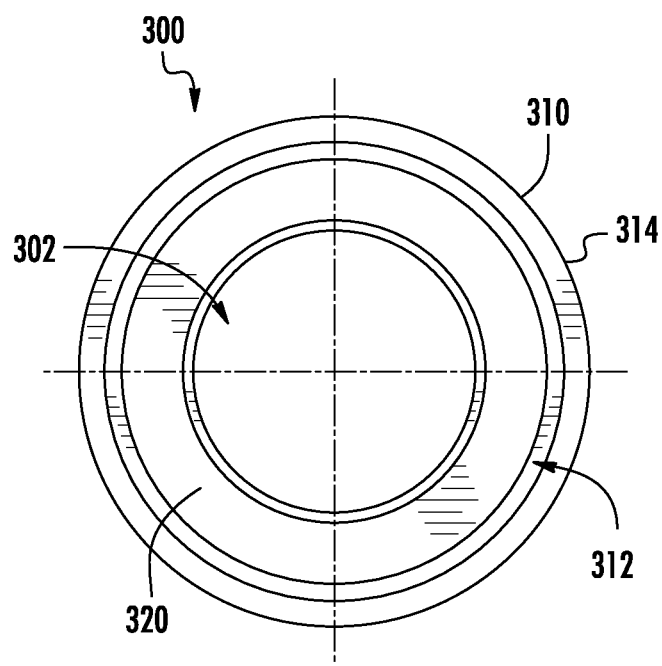
FIG. 8B illustrates a top view of the compressible member shown in FIG. 8A.
Figure 8C:
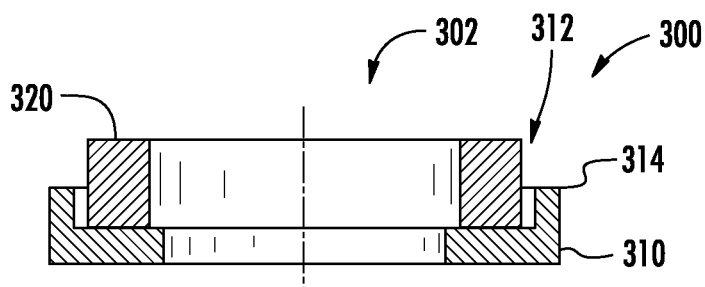
FIG. 8C illustrates a cross-sectional view of the compressible member shown in FIG. 8A, the cross-sectional view taken alone line 8C-8C in FIG. 8B.

Referring to FIGS. 8A-8C, another example of an embodiment of a dynamic segment 300 for enabling the proximal body portion 110 and the distal body portion 130 to axially translate relative to one another is disclosed. As shown, the dynamic segment 300 includes a containment cup 310 and a compressible member 320. In use, the dynamic segment 300 is positioned between the proximal body portion 110 and the distal body portion 130. The dynamic segment 300 may include an opening 302 for enabling the threaded rod 170 to pass therethrough as generally illustrated in FIG. 4, although other suitable mechanisms for holding, positioning, etc. the dynamic segment 300 between the proximal body portion 110 and the distal body portion 130 is envisioned.

As shown, the containment cup 310 and the compressible member 320 may have corresponding circular shapes, although other suitable shapes are envisioned. In use, the containment cup 310 may include a pocket 312 defined by, for example, a ledge 314 projecting along an outer circumference thereof. The pocket 312 being arranged and configured to receive at least a portion of the compressible member 320. In one embodiment, the containment cup 310 may be made from a substantially rigid material such as, for example, a metal such as stainless steel, titanium, etc. The compressible member 320 may be manufactured from a softer, compressible material such as, for example, a silicone, rubber, elastomer, etc. Thus arranged, in use, the compressible member 320 can be compressed thus facilitating axial movement of the proximal body portion 110 and the distal body portion 130 relative to each other. As will be appreciated by one of ordinary skill in the art, by controlling the extent by which the compressible member 320 extends beyond the ledge 314 of the containment cup 310, one can control the amount of compression and thus axial movement. That is, the extent or distance that the compressible member 320 extends beyond the containment cup 310 dictates the amount of axial movement provided. Thus arranged, by positioning at least a portion of the compressible member 320 within the containment cup 310, the amount of compression/axial movement can be controlled while protecting the compressible member from an overstressed situation.

In use, it is envisioned that the dynamic segment 200 may provide 0.1 to 5 millimeters of movement.

Orthopedic implants and prosthetics such as reconfigurable bone adjustment devices described herein typically are formed of a biocompatible metal. Medical grade cobalt-chromium (CoCr) alloys such as cobalt-chromium-molybdenum (CoCrMo) and cobalt-chromium-iron (CoCrFe) are among the most suitable metallic biomaterials, particularly for weight-bearing implants. These alloys typically exhibit high mechanical properties, adequate corrosion resistance, and acceptable biocompatibility. In one embodiment, a reconfigurable bone adjustment device according to the present disclosure is formed of a cobalt-chromium-iron (CoCrFe) alloy. In another embodiment, the alloy comprises a 40Co-20Cr-16Fe-15Ni-7Mo alloy. It should be appreciated however that the reconfigurable bone adjustment devices may be manufactured from any suitable material.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A reconfigurable bone adjustment device comprising:
   a first member configured for attachment to a first bone fragment;
   a second member configured for attachment to a second bone fragment;
   a drive mechanism configured to move the second member relative to the first member;
   a threaded rod having a proximal end operatively coupled to the drive mechanism, and a distal end operatively coupled to the second member so that operation of the drive mechanism rotates the threaded rod and moves the second member relative to the first member; and
   a dynamic segment positioned between the first and second members to enable compression of the second member relative to the first member to stimulate bone growth;
   wherein the dynamic segment includes a compressible assembly including a compressible member sandwiched between first and second end plates, the compressible member being selected from one of a silicone and a rubber, and the first and second end plates being manufactured from a metallic material.

2. The reconfigurable bone adjustment device of claim 1, wherein the dynamic segment is positioned within the first member.

3. The reconfigurable bone adjustment device of claim 1, wherein the dynamic segment is positioned adjacent to the drive mechanism.

4. The reconfigurable bone adjustment device of claim 1, wherein the compressible member is molded to the end plates.

5. The reconfigurable bone adjustment device of claim 1, wherein the compressible assembly including the compressible member and the first and second end plates include an opening formed therein for enabling the threaded rod to pass therethrough.

6. A reconfigurable bone adjustment device comprising:
   a first member configured for attachment to a first bone fragment;
   a second member configured for attachment to a second bone fragment;
   a drive mechanism configured to move the second member relative to the first member;
   a threaded rod having a proximal end operatively coupled to the drive mechanism, and a distal end operatively coupled to the second member so that operation of the drive mechanism rotates the threaded rod and moves the second member relative to the first member; and
   a dynamic segment positioned between the first and second members to enable compression of the second member relative to the first member to stimulate bone growth;
   wherein the dynamic segment includes a containment cup and a compressible member, the containment cup includes a ledge projecting along an outer circumference thereof, the ledge defining a pocket arranged and configured to receive at least a portion of the compressible member therein.

7. The reconfigurable bone adjustment device of claim 6, wherein the containment cup is manufactured from a metallic material, the compressible member is manufactured from one of a silicone or a rubber.

8. The reconfigurable bone adjustment device of claim 6, wherein the compressible member extends beyond the ledge of the containment cup.

9. The reconfigurable bone adjustment device of claim 6, wherein the dynamic segment is positioned within the first member.

10. The reconfigurable bone adjustment device of claim 6, wherein the dynamic segment is positioned adjacent to the drive mechanism.

\* \* \* \* \*